(12) United States Patent
Yu et al.

(10) Patent No.: US 7,723,044 B2
(45) Date of Patent: May 25, 2010

(54) METHODS AND APPARATUS FOR DETECTION OF VIRAL INFECTION

(75) Inventors: Yongyi Yu, Germantown, MD (US);
Lina Li, Rockville, MD (US);
Zhuangwu Li, Clarksville, MD (US);
Jun Bao, Hacienda Heights, CA (US)

(73) Assignee: Allied Biotech, Inc., Ijamsville, MD (US)

( * ) Notice: Subject to any disclaimer, the term of this patent is extended or adjusted under 35 U.S.C. 154(b) by 588 days.

(21) Appl. No.: 11/578,372

(22) PCT Filed: Apr. 12, 2005

(86) PCT No.: PCT/US2005/012019
§ 371 (c)(1),
(2), (4) Date: Oct. 13, 2006

(87) PCT Pub. No.: WO2005/118885
PCT Pub. Date: Dec. 15, 2005

(65) Prior Publication Data
US 2007/0212682 A1 Sep. 13, 2007

Related U.S. Application Data

(60) Provisional application No. 60/562,471, filed on Apr. 15, 2004.

(51) Int. Cl.
*G01N 33/53* (2006.01)
*A61K 39/12* (2006.01)

(52) U.S. Cl. .................. 435/7.1; 424/204.1; 424/159.1
(58) Field of Classification Search ...................... None
See application file for complete search history.

(56) References Cited

U.S. PATENT DOCUMENTS 6,448,387 B1* 9/2002 Slater et al. ................. 536/23.1
6,653,151 B2* 11/2003 Anderson et al. ............. 506/32

OTHER PUBLICATIONS

Wang et al. PNAS USA, 2002, 99(24):15687-15692.*
Opalka et al. Clinical and Diagnostic Laboratory Immunology, Jan. 2003, 10(1):108-115.*
Kingsmore et al. Current Opinion in Biotechnology, 2003, 14:74-81.*
The University of Chicago Animal Resources Center Mouse Specific Pathogen Free Criteria document accessed online at www.oicf.bsd.uchicago.edu/docs/MouseSpecificPathogenFree_Exclusion_List-1.pdf, dated Jun. 1, 2001.*

* cited by examiner

*Primary Examiner*—Stacy B Chen
(74) *Attorney, Agent, or Firm*—Andrews Kurth LLP (57) ABSTRACT

This invention generally relates to apparatus and methods for high-throughput, reproducible and inexpensive detection of virus infection using multiplexing technologies such as slide-based, microtiter plate-based and membrane-based microarrays and beads technologies. The apparatus and methods allow simultaneous detection of multiple viral infections in a plurality of test samples.

14 Claims, 7 Drawing Sheets

METHODS AND APPARATUS FOR DETECTION OF VIRAL INFECTION

RELATED APPLICATIONS

This application is the national phase entry of PCT application No. PCT/US05/12019, filed on Apr. 12, 2005, which claims the priority of U.S. Provisional Application No. 60/562,471 filed on Apr. 15, 2004, which is hereby incorporated by reference in its entirety.

BACKGROUND OF THE INVENTION

1. Field of the Invention

This invention generally relates to detection of viral infection and, in particular, to apparatus and methods for high-throughput, reproducible and inexpensive detection of virus infection using multiplexing technologies.

2. Background of the Technology

Virus infection can be detected with a number of conventional approaches, such as Enzyme-Linked Immunosorbent Assay (ELISA), Enzyme-linked immunoassay (EIA), and Western bolt, which typically detect the presence of a viral antigen or an antibody to a viral antigen. The limitations of conventional assays include low throughput, low automation, consumption of large amount of samples and reagents, and high assay cost. For example, a commonly used method for monitoring virus infections in laboratory mice and rats is an ELISA for detecting antivirus antibodies in the serum of the animal. The assay method, however, is time consuming and is capable of measuring only one antibody level per assay.

In recent years, multiplexed assays are gradually becoming a prevailing technology in the field of immunoassays, especially in the pharmacogenomics arena for drug discovery and clinical diagnostics purposes. The multiplexed assays allow simultaneous detection or quantification of multiple analytes from a single sample. One of the approaches to performing multiplexed assays is microarray, which was originally developed as a DNA/RNA based array system but has since evolved to include other array systems such as protein microarrays. Protein microarrays are compatible with hardware and software used by the DNA microarrays. Since protein microarrays facilitate the analysis of protein-protein, protein-ligand or protein-drug interactions, as well as enzymatic assays, they have been used in basic research and development, drug target identification and validation, drug screening, toxicity screening, lead optimization, and patient stratification for clinical trials and disease management (See, for example, Bussow. et al., Nucleic Acids Res, 26:5007-5008, 1998; Eisen et al., Methods Enzymol. 303:179-2000, 1999; Knezevic, et al., Proteomics, 1:1271-1278, 2001; Adam et al., Proteomics, 1:1264-1270, 2001; Zhu, et al., Current Opinion in Chemical Biology, 5:40-45, 2001; and Ronald et al., Proteome Research, 1:233-237, 2002).

In addition to various protein microarrays, other multiplexed analysis approaches of proteins include bead-based technology, which performs discrete bioassays of multiple proteins on the surface of fluorescent color-coded or differently sized beads known as microspheres. During the bioassays, those beads are read in a compact analyzer/flow cytometer, which simultaneously identifies the bioassays and measures the results, all in real time when sample is directly labeled with fluorophores.

While the multiplexed assay technologies, such as the micro arrays and beads technology, have been employed in many research and clinical applications, they have not been used for the monitoring viral infections in animals.

SUMMARY OF THE INVENTION

One aspect of the present invention relates to an inexpensive method for high-throughput detection of viral infection using multiplexing approaches, such as microarrays and bead technology. The method can be used for clinical diagnosis, animal surveillance, and research applications.

In one embodiment, the method comprises the steps of contacting a biological sample from the subject with a microarray system comprising a plurality of subarrays capable of capturing a plurality of target ligands, and detecting a captured target ligand by contacting the protein microarray system with a labeled anti-ligand that binds specifically to the captured target ligand. The presence of a target ligand in the biological sample is indicative of a viral infection in the subject, wherein the target ligands are either viral antigens or anti-virus antibodies and wherein the microarray system is capable of simultaneous detection of target ligands in a plurality of biological samples.

In a related embodiment, the protein microarray system is a chip-based microarray or a microtiter plate-based microarray.

In another related embodiment, the binding of the labeled anti-ligand to the captured target ligand is detected by fluorescence detection, chemiluminescence detection, or colorimetric detection.

In another embodiment, the method comprises the steps of incubating a biological sample from the subject with a labeled anti-ligand capable of forming a ligand/anti-ligand complex with a target ligand; contacting the incubated biological sample with a protein microarray system comprising a plurality of subarrays capable of capturing a ligand/anti-ligand complex, and detecting the captured ligand/anti-ligand complex. The presence of a target ligand in the biological sample is indicative of a viral infection in the subject, wherein the target ligand is either a viral antigen or an anti-virus antibody, and wherein the microarray system is capable of simultaneous detection of a plurality of target ligands in a plurality of biological samples.

In another embodiment, the method comprises the steps of contacting a biological sample from the subject with a protein subarray in a microarray system in the presence of a labeled target ligand standard, the labeled target ligand standard competes with a target ligand in the biological sample for binding to the protein subarray, and determining the presence of the target ligand in the biological sample based on a level of binding of the labeled target ligand standard to the protein subarray, wherein the microarray system comprises a plurality of protein subarrays and is capable of simultaneously capturing a plurality of target ligands in a plurality of samples, and wherein the target ligands comprises viral antigens and anti-virus antibodies.

In another embodiment, the method comprises the steps of contacting a biological sample from the subject with a membrane-based microarray comprising a plurality of anti-ligands capable of capturing a plurality of target ligands, and detecting a captured target ligand by contacting the membrane-based microarray with a labeled anti-ligand that binds specifically to the captured target ligand. The presence of a target ligand in the biological sample is indicative of a viral infection in the subject, wherein the target ligands are either viral antigens or anti-virus antibodies.

In another embodiment, the method comprises the steps of contacting a biological sample from the subject with a plurality of microbead species, each species of microbead is coated with an anti-ligand capable of capturing a target ligand in the biological sample; labeling a target ligand, the target ligand is either a viral antigen or an anti-virus antibody; and determining a binding of the target ligand and the microbeads. The target ligand can be labeled either before or after contacting with the plurality of microbead species, and the binding of the target ligand to the microbeads is indicative of a viral infection.

Another aspect of the present invention relates to microarray and bead system for detection of viral infection in a subject.

In one embodiment, the present invention provides a microarray system comprises a plurality of subarrays fabricated on a solid support. Each subarray comprises a plurality of anti-ligands immobilized to said solid support, and each anti-ligand is capable of specific binding to a target ligand that is either a viral antigen or an anti-virus antibody.

In a related embodiment, the solid support is in the form of a slide or a microtiter plate.

In another embodiment, the present invention provides a bead system comprises a plurality of microbead species, each species of microbead is coated with an anti-ligand capable of capturing a target ligand in the biological sample, wherein the target ligand is either a viral antigen or an anti-virus antibody.

In yet another embodiment, the present invention provides a kit for detection of viral infection in a subject. The kit comprises the microarray and/or the microbead system described above, and a labeling reagent capable of binding to the target ligand.

Additional aspects of the disclosure will be set forth in part in the description, will in part be obvious from the description, and/or may be learned from practicing the invention. The invention is set forth and particularly pointed out in the claims, and the disclosure should not be construed as limiting the scope of the claims. The following detailed description includes exemplary representations of various embodiments of the invention which are not restrictive of the invention as claimed. The accompanying figures constitute a part of this specification and, together with the description, serve to illustrate embodiments and not limit the invention.

BRIEF DESCRIPTION OF THE FIGURES

FIG. 1 is a schematic design of an animal surveillance slide with 8 subarrays per slide and a bar code. The filled and open spots denote 15 viral antigens (P1-P15, filled spots) and their respective negative controls (N1-N15, open spots) in duplicate. The hatched spots denote a positive control (C1) in duplicate and at different concentrations. In its current setting, each slide can be used to detect up to 8 serum-samples and up to 15 viruses in each sample. The bar code can be used to distinguish the array slides. Table 1 provides a representative list of possible viral antigens for a mouse surveillance slide.

FIG. 2 is a schematic design of animal surveillance chip with 16 subarrays per slide. Similar to FIG. 1, the filled and open spots denote 15 viral antigens (P1-P15, filled spots) and their respective negative controls (N1-N15, open spots) in duplicate. The hatched spots denote a positive control (C1) in duplicate and at different concentrations. In this setting, each slide can be used to detect up to 16 serum-samples and up to 15 viruses in each sample.

FIGS. 6A and 6B demonstrate the specificity of the mouse surveillance microarray slide of FIG. 1.

FIGS. 7A and 7B demonstrate multiplex detection of a mouse surveillance microarray slide by a colorimetric scanner.

FIGS. 8A and 8B show multiplex detection of mouse surveillance microarray by a fluorescent laser scanner (ScanArray 3000, General Scanning, Watertown, Mass.).

FIGS. 9A and 9B show comparison between colorimetric and fluorescent detection of viral infection using mouse surveillance microarrays. Two identical microarray slides were used for calorimetric and fluorescent detection of anti-virus antibodies in the same mouse serum, respectively. Signals are averaged upon duplicated spots of each viral antigen and its negative controls.

FIGS. 11A-11C show multiplex detection of mouse antisera with 96-well microtiter plate-based microarrays.

1—incubation with an antisera followed with biotinylated goat-anti mouse antibody (1.0 ug/ml) and streptavidin-Cy5 (1.0 ug/ml);

2—incubation with an antisera followed with biotinylated goat-anti mouse antibody (0.1 ug/ml) and streptavidin-Cy5 (1.0 ug/ml);

3—incubation with an antisera followed with biotinylated goat-anti mouse antibody (10 ug/ml) and streptavidin-Cy5 (10 ug/ml);

4—incubation with an antisera followed with biotinylated goat-anti mouse antibody (1.0 ug/ml) and streptavidin-Cy5 (1.0 ug/ml);

DETAILED DESCRIPTION OF THE INVENTION

Definitions

As used herein, the term "animal virus" refers to any virus that is capable of reproduction or propagation in an animal host cell. Animal viruses include, but are not limited to, viruses from human, orangutan, gorilla, chimpanzee, monkey, mouse, rat, dog, donkey, cat, cattle, horse, chicken, duck, pig, and cow.

As used herein, the term "biological sample" refers to biological samples in any form such as whole blood, sera, plasma, urine, saliva, feces, spinal fluids, cells and tissues, etc.

As used herein, the term "ligand" refers to one member of a ligand/anti-ligand binding pair. The ligand may be, for example, one of the nucleic acid strands in a complementary, hybridized nucleic acid duplex binding pair; an effector or receptor molecule in an effector/receptor binding pair; or an antigen or antibody in an antigen/antibody binding pair.

As used herein, the term "anti-ligand" refers to the opposite member of a ligand/anti-ligand binding pair. The anti-ligand may be the other of the nucleic acid strands in a complementary, hybridized nucleic acid duplex binding pair; the receptor or effector molecule in an effector/receptor binding pair; or an antigen or antibody in an antigen/antibody binding pair.

An "antibody," as used herein, means a polyclonal or monoclonal antibody. Further, the term "antibody" means intact immunoglobulin molecules, chimeric immunoglobulin molecules, or Fab or F(ab')$_2$ fragments. Such antibodies and antibody fragments can be produced by techniques well known in the art which include those described in Harlow and Lane (Antibodies: A Laboratory Manual Cold Spring Harbor Laboratory, Cold Spring Harbor, N.Y. (1989)) and Kohler et al., (Nature 256: 495-97 (1975)) and U.S. Pat. Nos. 5,545,806, 5,569,825 and 5,625,126, incorporated herein by reference. Correspondingly, antibodies, as defined herein, also include single chain antibodies (ScFv), comprising linked $V_H$ and $V_L$ domains and which retain the conformation and specific binding activity of the native idiotype of the antibody. Such single chain antibodies are well known in the art and can be produced by standard methods. (see, e.g., Alvarez et al., Hum. Gene Ther. 9: 229-242 (1997)). The antibodies of the present invention can be of any isotype IgG, IgA, IgD, IgE and IgM.

An "anti-virus antibody," as used herein, include antibodies that specifically bind to a viral antigen.

An "antigen," as used herein, includes substances that upon administration to a vertebrate are capable of eliciting an immune response, thereby stimulating the production and release of antibodies that bind specifically to the antigen. Antigen, as defined herein, includes molecules and/or moieties that are bound specifically by an antibody to form an antigen/antibody complex. In accordance with the invention, antigens may be, but are not limited to, peptides, polypeptides, proteins, nucleic acids, DNA, RNA, saccharides, combinations thereof, fractions thereof, or mimetics thereof.

A "viral antigen," as used herein, include an antigen derived from a virus, and any antigenic substance that is capable of eliciting an immune response to an antigen derived from a virus, thereby stimulating the production and release of antibodies that bind specifically to the antigen derived from a virus.

"Mimetic," as used herein, includes a chemical compound, or an organic molecule, or any other mimetic, the structure of which is based on or derived from a binding region of an antibody or antigen. For example, one can model predicted chemical structures to mimic the structure of a binding region, such as a binding loop of a peptide. Such modeling can be performed using standard methods. In particular, the crystal structure of peptides and a protein can be determined by X-ray crystallography according to methods well known in the art. Peptides can also be conjugated to longer sequences to facilitate crystallization, when necessary. Then the conformation information derived from the crystal structure can be used to search small molecule databases, which are available in the art, to identify peptide mimetics which would be expected to have the same binding function as the protein (Zhao et al., Nat. Struct. Biol. 2: 1131-1137 (1995)). The mimetics identified by this method can be further characterized as having the same binding function as the originally identified molecule of interest according to the binding assays described herein.

Alternatively, mimetics can also be selected from combinatorial chemical libraries in much the same way that peptides are (see e.g., Eichler et al., Med. Res. Rev. 15: 481-96 (1995); Blondelle et al., Biochem. J 313: 141-147 (1996); Perez-Paya et al., J. Biol. Chem. 271: 4120-6 (1996)).

An "array" broadly refers to an arrangement of agents (e.g., proteins, antibodies) in positionally distinct locations on a substrate. In some instances the agents on the array are spatially encoded such that the identity of an agent can be determined from its location on the array.

A "microarray" generally refers to an array in which detection requires the use of microscopic detection to detect complexes formed with agents on the substrate. A "location" or "spot" on an array refers to a localized area on the array surface that includes agents, each defined so that it can be distinguished from adjacent locations (e.g., being positioned on the overall array, or having some detectable characteristic, that allows the location to be distinguished from other locations). Typically, each location includes a single type of agent but this is not required. The location can have any convenient shape (e.g., circular, rectangular, elliptical or wedge-shaped). The size or area of a location can vary significantly. In some instances, the area of a location is greater than 1 cm$^{2+1}$, such as 2-20 cm$^{2+1}$, including any area within this range. More typically, the area of the location is less than 1 cm$^2$, in other instances less than 1 mm$^2$, in still other instances less than 0.5 mm$^2$, in yet still other instances less than 10,000 um$^2$, or less than 100 um$^2$. A "chip/slide-based microarray," as used herein, refers to a microarray fabricated on a solid support in the shape of a chip or slide.

A "microtiter plate-based microarray," as used herein, refers to a microarray fabricated on the bottom of a well of a microtiter plate, such as a 96-well microplate.

A "membrane-based microarray," as used herein, refers to a microarray fabricated on a supporting membrane, such as a nitrocellulose membrane.

A "solid support," as used herein, means any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The support material may have virtually any possible structural configuration so long as the coupled molecule is capable of binding to an antigen or antibody. Thus, the support configuration may be spherical, as in a bead, or cylindrical, as in the inside surface of a test tube or a microtiter plate well. Alternatively, the surface may be flat such as a sheet, membrane, test strip, chip, slide, etc. Preferred supports include nitrocellulose membrane, nitrocellulose-coated slides, 96-well microtiter plates, and polystyrene or carboxyl beads. Those skilled in the art would understand that many other carriers are suitable for binding antibody or antigen, or will be able to ascertain the same by use of routine experimentation.

The phrase "a plurality of . . ." as used herein, refers to two or more species in a genus. For example, a plurality of antigens refers to two or more antigens.

The phrases "specifically binds," "specific binding affinity" (or simply "specific affinity"), "specifically recognize," and other related terms when used to refer to binding between a protein and an antibody, refers to a binding reaction that is determinative of the presence of the protein in the presence of a heterogeneous population of proteins and other biologics. Thus, under designated conditions, a specified antibody binds preferentially to a particular protein and does not bind in a significant amount to other proteins present in the sample. An antibody that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein (See, e.g., Harlow and Lane (1988) Antibodies, A Laboratory Manual, Cold Spring Harbor Publications, New York, for a description of immunoassay formats and conditions that can be used to determine specific immunoreactivity).

A "label" refers to an agent that can be detected by using physical, chemical, optical, electromagnetic, electrochemical and/or other methods. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

Microarray and Bead System for Viral Detection

The present invention provides multiplexed approaches for detection of virus infection using microarrays and beads-based technology. One aspect of the present invention relates to an inexpensive apparatus for high-throughput detection of viral infection using multiplexing approaches, such as chip-based microarrays, microtiter plate-based microarrays, membrane-based microarrays, and bead technology. The apparatus can be used for animal surveillance, research and diagnostic applications.

In one embodiment, the present invention provides a microarray system capable of simultaneous detection of a plurality of target ligands in a plurality of test samples. The microarray system comprises anti-ligands immobilized on a solid support in the form of chip-based microarrays, microtiter plate-based microarrays, and membrane-based microarrays. The anti-ligands are capable of specific binding to target ligands, such as viral antigens and anti-viral antibodies.

The microarray of the present invention can be fabricated with any format on a suitable solid support (i.e., a substrate). Examples of suitable solid support include, but are not limited to, chemically coated or non-coated glass, and polymer slides, various types of membranes made from polyvinylidene fluoride (PVDF), nitrocellulose, nylon and/or other suitable materials, such as Biotrans (ICN), Zeta-probe (Bio-Rad), Colony/Plaque Screen (NEN), Hybond-N$^+$ (Amersham), Magnacharge (MSI), Magnagraph (MSI) and Hybond ECL (Amersham), chemically modified or non-modified silicon wafers, various types of microtiter plates made of polystyrene with or without coating, polymer surfaces, porous filters made of metal oxides or others, and hydrogel.

Other examples of solid support material include silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for solid support material of the array. In addition, many ceramics and polymers may also be used as solid support material. Polymers which may be used as solid support material include, but are not limited to, the following: polystyrene; poly(tetra)fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polypropylethylene, polyethylene; polyhydroxyethylmethacrylate (HEMA); polydimethylsiloxane; polyacrylamide; polyimide; and block-copolymers. Preferred solid support material for the array include silicon, silica, glass, and polymers. The solid support material on which the binding molecules reside may also be a combination of any of the aforementioned substrate materials Geometry of solid support includes 2-dimensional planar or flat surface materials, 3-dimensional flow-through silicon and glass wafers, as well as porous filters or hydrogels. All those solid support can be used with or without additional supportive materials for multiplexed detection of viral infection. The solid support may be fabricated inside a cartridge for applications and operations in manual, semi-automatic or automatic modes.

The anti-ligands include, but are not limited to, viral antigens, antivirus antibodies, or any other molecules capable of capturing/specific binding to a viral antigen or antivirus antibody, such as the aptamers of SomaLogic, Inc. (Boulder, Colo.). Aptamer is a single-stranded oligonucleotide (generally DNA for diagnostic applications) that assumes a specific, sequence-dependent shape and binds to a target protein based on a lock-and-key fit between the two molecules. Aptamers are identified using the RLINK"http://www.somalogic.com/glossary/glossary.html"\l"selprocess"SELEX process.

The anti-ligands may be immobilized on the solid support through covalent or non-covalent interactions between various functional groups. A detailed discussion on immobilization technologies can be found in, for example, U.S. Pat. Nos. 6,329,209 and 6,305,418, which are hereby incorporated by reference in their entirety.

An array of the present invention may optionally further comprise a coating between the solid support material and the binding molecules (i.e., the anti-ligands). This coating may either be formed on the solid support material or applied to the solid support material. The solid support material can be modified with a coating by using thin-film technology based, for instance, on physical vapor deposition (PVD), plasma-enhanced chemical vapor deposition (PECVD), or thermal processing. Alternatively, plasma exposure can be used to directly activate or alter the solid support material and create a coating. For instance, plasma etch procedures can be used to oxidize a polymeric surface (for example, polystyrene or polyethylene to expose polar functionalities such as hydroxyls, carboxylic acids, aldehydes and the like) which then acts as a coating.

the anti-ligands can be deposited on the solid support by microspotting. Microspotting encompasses deposition technologies that enable automated microarray production by printing small quantities of pre-made biochemical substances onto solid surfaces. Printing is accomplished by direct surface contact between the surface of a solid support and a delivery mechanism, such as a pin or a capillary. Robotic control systems and multiplexed printheads allow automated microarray fabrication. The anti-ligands can also be deposited on the solid support by non-contact dispensing with piezo-electric ceramics or microsolenoid valves. Other technologies for microarray production include photolithography and ink jet technologies. Methods for fabricating microarrays are described in, for example, U.S. Pat. No. 5,807,522 to Brown et al., U.S. Pat. No. 6,110,426 to Shalan et al., and U.S. Pat. No. 6,139,831 to Shivashankar et al., which are hereby incorporated by reference in their entirety.

Depending on the application, a single microarray may be immobilized with antibodies to, or antigens from, dozens or even hundreds of viruses, and multiple viral-specific antibodies/antigens may be used for each virus. The spots on the microarray may each represent a different species of protein or that the multiple spots on the microarray may represent the same species of protein. Different antibodies to, or antigens from, the same virus may be spotted individually or in a mixture. As is well-known to one skilled in the art, positive and negative controls are also included in each microarray. Concentrations of antibodies/antigens deposited on microarrays will be optimized in terms of dynamic ranges, assay sensitivity and specificity. Immobilization efficiency of proteins on a solid support depends on various factors including concentration of the proteins, immobilization time and post-spotting environments (temperature and humidity, etc), and storage conditions (temperature and humidity, etc).

In one embodiment of the invention, the microarray of the present invention has a density of at least 5 spots/cm$^2$, preferably at least 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000, 9000 or 10,000 spots/cm$^2$.

Figure 1:
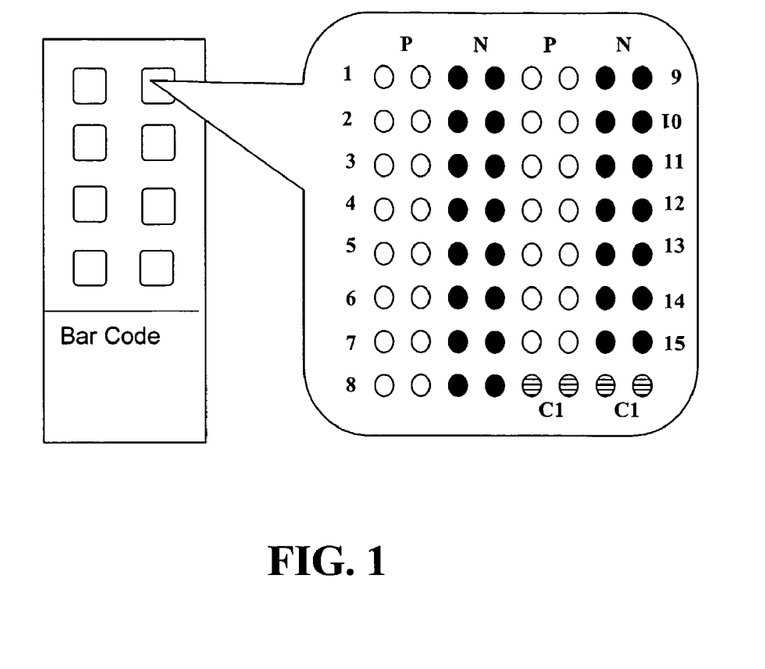
Figure 2:
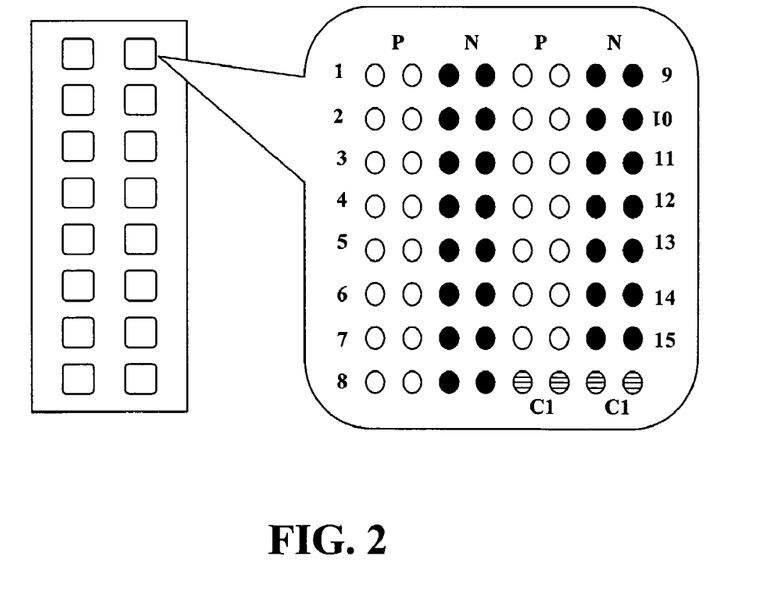

In another embodiment, multiple microarrays are fabricated on a single slide or chip for simultaneous detection of viral infection in multiple samples. FIG. 1 shows a representative animal virus detection slide that can be used to detect up to 8 serum samples and up to 15 virus infections in each sample. FIG. 2 shows a slide with a more compact format that allows the detection of up to 16 serum samples and up to 15 virus infections in each sample. Table 1 shows a representative list of viral antigens for a mouse surveillance microarray chip. Typically, each viral antigen and its negative control are present in duplicate. The array would also include positive controls that react with the labeling system in the absence of a target ligand. The detection slide optionally contains a bar code that is used to identify the slide.

| Positive Antigen | Negative Antigen | Viral Antigen Description |
|---|---|---|
| P1 | N1 | MHV (Mouse hepatitis virus) |
| P2 | N2 | MVM (Minute virus of mice) |
| P3 | N3 | PVM (Pneumonia virus of mice) |
| P4 | N4 | Sendai (Parainfluenza 1) |
| P5 | N5 | Polyoma |
| P6 | N6 | Ectromelia (Mouse pox) |
| P7 | N7 | Reovirus 3 |
| P8 | N8 | TMEV (Theiler's virus, GD VII) |
| P9 | N9 | EDIM (Mouse rotavirus) |
| P10 | N10 | MSGV (Mouse cytomegalovirus) |
| P11 | N11 | Murine herpesvirus 68 |
| P12 | N12 | Mouse adenovirus (FL) |
| P13 | N13 | Mouse adenovirus (K87) |
| P14 | N14 | LCM (Lymphocytic choriomeningitis) |

In another embodiment, the microarrays of the present invention are fabricated on the bottom of a well of 96-well microtiter plate, such as Corning® 96-well polystyrene High Bind Microplate (black with clear flat bottom). Desired features of the microtiter plate for protein microarray fabrication include high affinity binding surface for medium and large biomolecules (>10 kD) that possess ionic groups and/or hydrophobic regions; and large binding capacity in the range of 100 to 200 ng IgG/cm$^{2+1}$, preferably in the range of 300 to 600 ng IgG/cm$^{2+1}$, and more preferably in the range of 400 to 500 ng IgG/cm$^2$. The microtiter plates suitable for microarray fabrication should have thin well bottoms that provide lower background fluorescent and allow reading wavelengths down to 340 nm. The plates should also be designed to reduce well-to-well crosstalk during fluorescent assays, conform to standard microplate footprint and dimensions, and suitable for use in both top and bottom reading instruments. The microtiter plate wells may have a working volume of 25 to 400 μl, preferably 75 to 200 μl.

Fabrication of microarray on a microtiter plate is described in e.g., U.S. Pat. No. 6,803,238, which is hereby incorporated by reference in its entirety. The microtiter plate-based microarrays can be used to detect viral infection in a high-throughput mode and are easily adaptable to standard plate-based ELISA automatic processes, such as sample or reagent delivery, incubation and washing steps.

In another embodiment, the microarray of the present invention is fabricated on a membrane support, such as a nitrocellulose membrane.

Methods for Viral Detection Using the Microarray

Another aspect of the present invention relates methods for detecting viral infection using the microarray of the present invention. Typically, the microarray is incubated with a test sample to capture any target ligand in the test sample. The presence of one or more target ligands is indicative of one or more virus infections in the subject from which the test sample is obtained.

Figure 3:
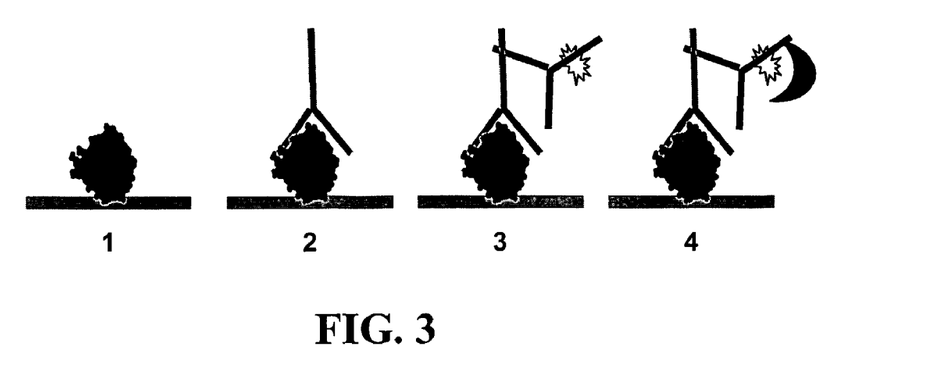
FIG. 3 is a schematic of an "antigen-down" immunoassay using a protein microarray or microbeads.

In one embodiment, the target ligands are anti-virus antibodies and the ligands are captured through a so-called "antigen-down" immunoassay. As shown in FIG. 3, the anti-ligands on the microarray comprises immobilized viral antigens. Each array spot may comprise an immobilized viral antigen or mixture of viral antigens on each array spot. A first incubation allows a virus-specific antibody in a test sample (e.g., a animal serum) to be captured by the immobilized viral antigen on the array surface. The second incubation allows the labeled secondary antibody to bind to the captured virus-specific antibody and produce a signal on the corresponding array spot.

Depending on the nature of the detection technique utilized, labeled target protein or various labeled detection reagents (e.g., labeled antibodies or labeled packages) can be used to detect the formation of a complex between a target protein and package/antibody reagent. A variety of different labels can be utilized in these detection schemes. The proteins, antibodies or packages can be labeled with any of a variety of different types of labels, provided the label does not interfere with the formation of a complex between a package/antibody reagent and a target protein and can generates a detectable signal once such a complex is formed. Suitable labels include, but are not limited to, radiolabels, chemiluminescence labels, chromophores, electron dense agents, NMR spin labels, a chemical tag suitable for detection in a mass spectrometer, agents detectable by infrared spectroscopy or NMR spectroscopy, and enzyme substrates or cofactors for example. Radiolabels, particularly for spatially resolved proteins, can be detected using phosphor imagers and photochemical techniques.

Certain methods utilize fluorophores since various commercial detectors for detecting fluorescence from labeled proteins are available. A variety of fluorescent molecules can be used as labels including, for example, fluorescein and fluorescein derivatives, rhodamine and rhodamine derivatives, naphythylamine and naphthylamine derivatives, benzamidizoles, ethidiums, propidiums, anthracyclines, mithramycins, acridines, actinomycins, merocyanines, coumarins, pyrenes, chrysenes, stilbenes, anthracenes, naphthalenes, salicyclic acids, benz-2-oxa-1-diazoles (also called benzofurazans), fluorescamines and Bodipy dyes.

While fluorescence labeling has been widely used in microarray technologies owing to the benefits from stable and inexpensive fluorophores, high sensitivity and environmental safety, fluorescence detection requires expensive instrumentation. Moreover, the auto-fluorescence on chip surface, which causes higher background and lower signal to noise ratio, also limits the application of fluorescence in microarray technologies. Novel detection strategies such as colorimetric imaging provide an alternative detection method on multiplexed microarray-based systems. One of the attractive features of colorimetric detection is the low background. In fluorescence imaging, an excitation source is needed and certain amount of signals are generated in areas of the microarray where the fluorophore is not present. In colorimetric imaging, however, photons are generated only where the reactants such as labeling enzymes are present. Consequently, nonspecific radiation is significantly reduced. Moreover, colorimetric imaging does not have the excitation source-related problems, such as warm-up and drift of the light source, and interference from light scattering.

Another attractive feature of colorimetric detection is its low cost (a CCD-based colorimetric scanner with associated software for image capture and analysis costs at a fraction of a comparable fluorescent scanning equipment). Complementing fluorescent scanning technology, the colorimetric system allows researchers to use the full spectrum of pigmented labels including the products of horseradish peroxidase (HRP), alkaline phosphatase (AP), gold-silver developers, and any other labeling system that produces a pigmented reaction precipitate.

In a preferred embodiment, the captured antivirus antibody in a "antigen-down" microarray is detected by using a biotinylated or enzyme-labeled secondary antibody followed by incubation with a streptavidin-fluorophore conjugate (for fluorescence detection) or an enzyme substrate (for calorimetric detection).

Figure 4:
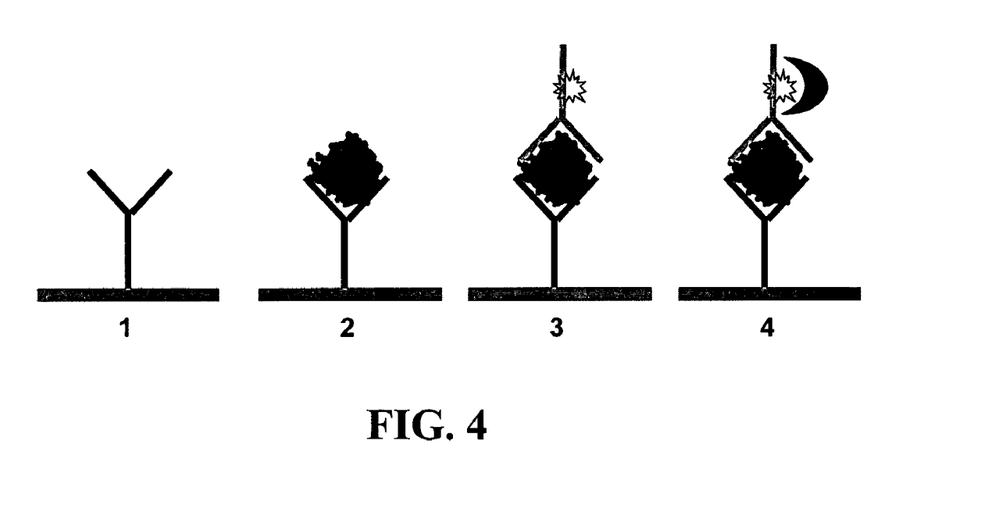
FIG. 4 is a schematic of a "sandwich" immunoassay using a protein microarray or microbeads.

In another embodiment, the present invention provides an antibody microarray containing immobilized viral antigen-specific antibodies on its surface. As shown in FIG. 4, the microarray can be used in a "sandwich" assay in which the antibody on the microarray captures a specific antigen (e.g., a viral surface antigen) in the test sample and the captured antigen is detected by a labeled secondary antibody that specifically binds to the captured viral antigen. In a preferred embodiment, the secondary antibody is biotinylated or enzyme-labeled. The detection is achieved by subsequent incubation with a streptavidin-fluorophore conjugate (for fluorescence detection) or an enzyme substrate (for colorimetric detection).

Typically, a multiplexed assay contains multiple incubation steps, including incubation with the samples and incubation with various reagents (e.g., primary antibodies, secondary antibodies, reporting reagents, etc.). Repeated washes are also needed between the incubation steps. The multiplexed assays of the present invention may be performed in a fast assay mode that requires only one or two incubations. For example, an antigen microarray may be first incubated with the samples, and then with a mixture of the primary and secondary antibodies, or with a mixture of the primary antibodies, the secondary antibodies, and the staining reagents. It is also conceivable that the formation of a detectable immune complex (e.g., a captured antivirus antibody/anti-Ig/label complex) may be achieved in a single incubation step by exposing the protein microarray to a mixture of the sample and all the necessary reagents.

Figure 5:
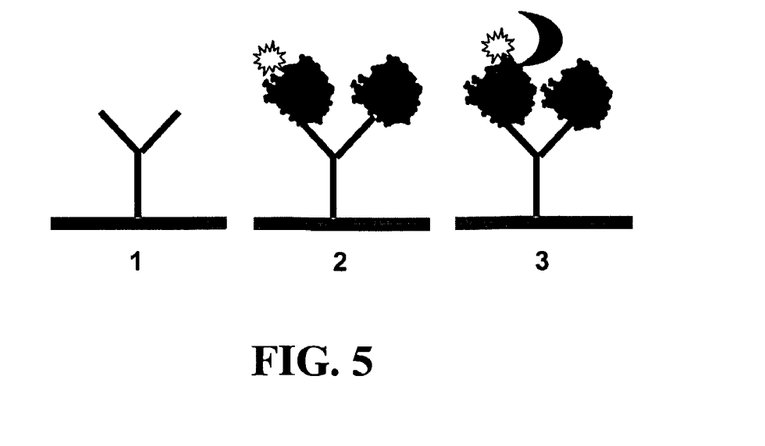
FIG. 5 is a schematic of a competitive immunoassay using a protein microarray or microbeads.

In yet another embodiment, the present invention provides a competitive immunoassay using an antibody microarray. Briefly, a microarray comprising immobilized antivirus antibodies is incubated with a test sample in the presence of a labeled viral antigen standard (FIG. 5). The labeled viral antigen competes with the unlabeled viral antigen in the test sample for the binding to the immobilized antigen-specific antibody. In such a competitive setting, an increased concentration of the specific viral antigen in the test sample would lead to a decreased binding of the labeled viral antigen standard to the immobilized antibody and hence a reduced signal intensity from the label.

The microarrays of the present invention can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, an antigen microarray can be processed with a ProteinArray Workstation (PerkinElmer Life Sciences, Boston, Mass.) or Assay 1200™ Workstation (Zyomyx, Hayward, Calif.).

Various optical devices, including CCD cameras or PMT or CCD line scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package. For example, quantification of an antigen microarray can be achieved with a fluorescent PMT-based scanner—ScanArray 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. To speed up whole assay process from capturing an image to generating an assay report, all the analytical steps including image capture, image analysis, and report generation, can be confined in and/or controlled by one software package. Such an unified control system would provide the image analysis and the generation of assay report in a user-friendly manner.

Beads System and Assay Method

Anther aspect of the present invention relates to utilization of bead-based immunoassays for the detection of viral infections. In a bead-based assay, the molecular reactions take place on the surface of microscopic beads. The beads can be made of a variety of materials such as polystyrene, physically or chemically modified glass, silicon, metal oxides, and other materials having surfaces containing carboxyl groups.

The target ligands (e.g., viral antigens or anti-virus antibodies) can be covalently immobilized on carboxylated (COOH) bead surface by amine coupling with reagents, such as 1-ethyl-3-(3-dimethylaminopropyl)carbodiimide (EDC) and N-hydroxysulfosuccinimide (S—NHS). Other approaches include immobilizing antigens or antibodies on bead surfaces containing aldehyde or epoxy groups. The antigens or antibodies may also be non-covalently immobilized on high-protein binding bead surface, such as surfaces coated with various polymers.

The beads are internally color-coded with fluorescent dyes and the surface of the bead is tagged with an anti-ligand (e.g., a viral antigen or an anti-virus antibody) that can bind a target ligand in a test sample. The target ligand, in turn, is either directly labeled with a fluorescent tag or indirectly labeled with an anti-ligand conjugated to a fluorescent tag. Hence, there are two sources of color, one from the bead and the other from the fluorescent tag. Alternatively, the beads can be internally coded by different sizes.

By using a blend of different fluorescent intensities from the two dyes, as well as beads of different sizes, the assay can measure up to hundreds of different target ligands. During the assay, a mixture containing the color/size-coded beads, fluorescence labeled anti-ligands, and the sample are combined and injected into an instrument that uses precision fluidics to align the beads. The beads then pass through a laser and, on the basis of their color or size, either get sorted or measured for color intensity, which is processed into quantitative data for each reaction.

When samples are directly labeled with fluorophores, the system can read and quantitate only fluorescence on beads without removing unbound fluorophores in solution. The assays can be multiplexed by differentiating various colored or sized beads. Real time measurement is achievable when a sample is directly labeled with fluorophores. Typically, a fluorophores-labeled secondary antibody is required for unlabeled samples. Standard assay steps include incubation of a sample with anti-ligand coated beads, incubation with biotin or fluorophore-labeled secondary antibody, and detection of fluorescence signals. Fluorescent signals can be developed on bead (by adding streptavidin-fluorophore conjugates for biotinylated secondary antibody) and read out by a bead analyzer. Depending on the anti-ligand immobilized on the bead surface, a bead-based immunoassay can be an antigen-down type (FIG. 3), a sandwich type (FIG. 4), or a competitive type (FIG. 5) immunoassay.

Kits

The present invention also relates to a viral detection kit that contains (1) a microarray-based viral infection detection system and/or a bead-based viral infection detection system as described above, and (2) one or more reagents required for performing the detection assay. The reagents may include, but are not limited to, labeled secondary antibodies, labeled antigens, enzyme substrates, blocking reagents, and washing buffers.

As described herein, the microarray and bead system of the present invention can be used for the detection of virus infection in humans and animals. Table 1 provides a representative list of murine viruses that can be detected by the microarray and bead system of the present invention. One skilled in the art would understand that the microarray and bead system of the present invention can be used for the detection of viral infections in humans caused by, for example, human immunodeficiency virus (HIV), herpes simplex virus (HSV, chickenpox virus (varicella-zoster virus or VZV), respiratory syncytial virus (RSV), Epstein-Barr virus, cytomegalovirus (CMV), rotavirus, hepatitis viruses, human papillomavirus (HPV), and influenza virus. It is also conceivable to use the microarray and bead system of the present invention for detection of viral infection in other laboratory animals such as rats, rabbits, ferrets, and guinea pigs, in farm animals such as horses, cattle, sheep, goats, pigs, turkeys, chicken, ducks, geese, elk and llamas, and in pets such as cats and dogs. For example, a rat surveillance microarray may be manufactured to detect infections caused by Kilham rat virus (KRV), reo virus type 3 (REO 3), rat pneumonia virus (PVM), sendai virus, sialodacroadenitis virus (SDAV), mouse adenovirus (MAD FL), lymphocytic choriomeningitis virus (LCMV), encephalomyelitis virus (GD VII), and Toolan H1 virus (H1). Similarly, a cattle surveillance microarray may be manufactured to detect viral diseases such as foot and mouth disease, enzootic bovine leucosis, blue tongue, epizootic, haemorrhagic disease of deer, rinderpest, Arkabane disease, bovine viral diarrhea-mucosal disease, infectious bovine rhinotracheitis, paratuberculosis, brucellosis, tuberculosis, bovine campylobacteriosis, and anthrax.

EXAMPLES

Example 1

Mouse Surveillance Microarray

An antigen microarray was produced for simultaneous detection of up to 14 virus infections in mouse serum. The microarray was fabricated by depositing 14 viral antigens and their negative controls, both of which are commercial products (Churchill Applied Biotechnology Ltd, UK) in a layout as shown in FIG. 1 and Table 1. Viral antigens were derived from cell or egg culture along with extracts from that culture and medium. Negative controls were prepared in an identical fashion with the exception that the culture was not seeded with virus. Nitrocellulose-coated slides (Schleicher & Shcuell Bioscience, Inc., Keene, N.H.) were used as chip substrates. A mouse immunoglobin G (IgG) was used as the positive controls. Spotted chips were air-dried for 2 hours and ready for use.

Example 2

Specificity of the Mouse Surveillance Microarray

Figure 6A:
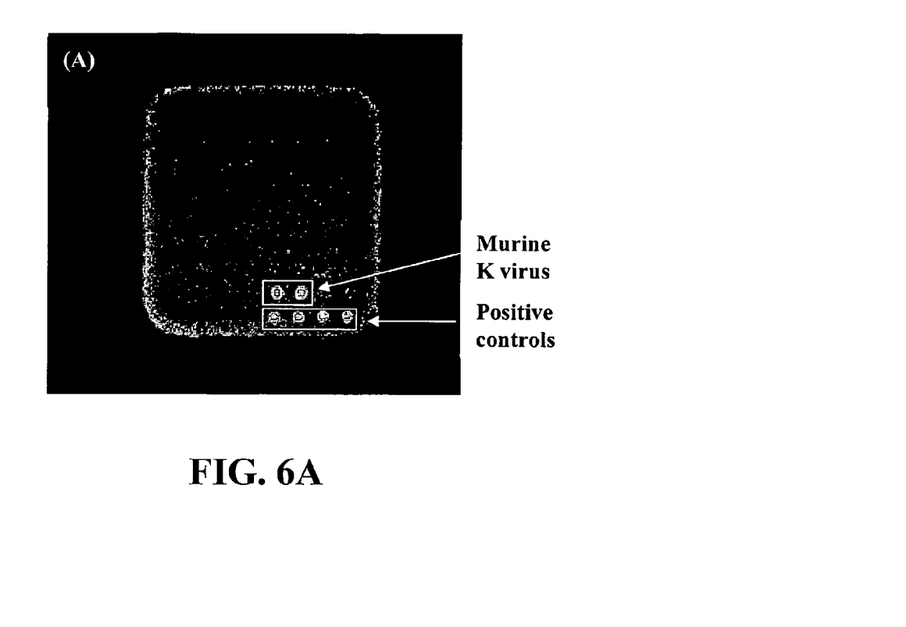
FIG. 6A is an image of a subarray with a positive signal for murine K virus. The subarray has a viral antigen layout as shown in FIG. 1 and Table 1, with a viral antigen for murine K virus at position P15 and corresponding negative control at position N15. The subarray was incubated with a mouse serum sample containing antibody to murine K virus.
Figure 6B:
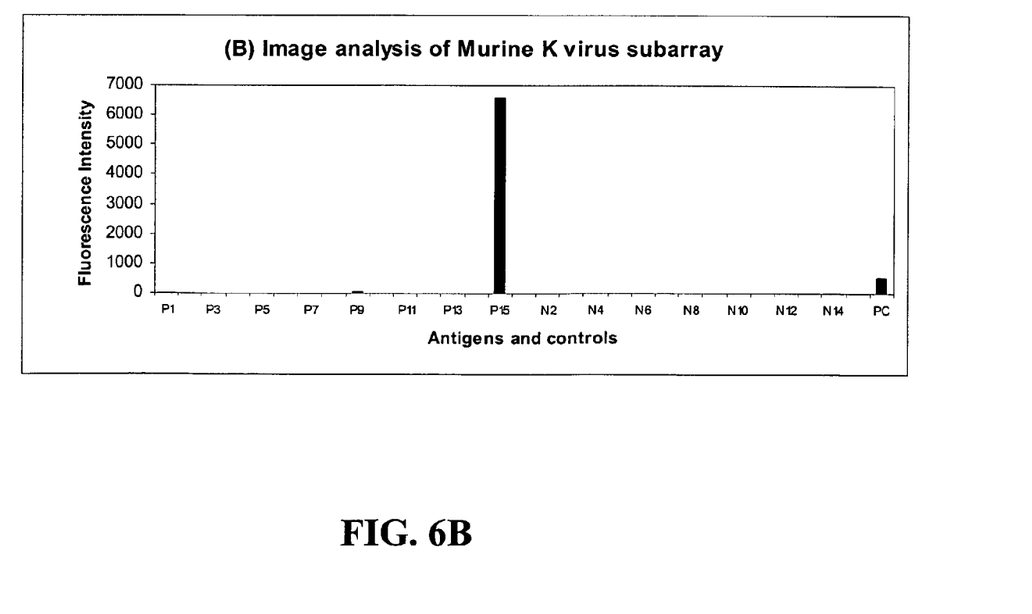
FIG. 6B shows image analysis of the murine K virus microarray of FIG. 6A. P1 and N1 denote viral antigen 1 and its negative control in Table 1, and so on for other antigens.

Prior to loading infected mouse antisera (Churchill Applied Biotechnology Ltd, UK), the mouse surveillance microarray was incubated with Tris-buffer (pH 7.2) for 15 minutes to wash away non-bounded antigens. The mouse surveillance microarray was then incubated for 2 hours at room temperature with 30 ul of an anti-murine K virus mouse serum at a 1:1600 dilution with Tris-buffered saline, pH7.2. The microarray washed after the first incubation, incubated with a biotinylated goat anti-mouse antibody for 1 hour, washed again, and then incubated with streptavidin-Cy5 conjugate for 30 minutes. The fluorescence image was captured by a fluorescent scanner and analyzed with image analysis software. As shown in FIG. 6A, only the murine K virus and the positive control spots were lit up after the incubations. The fluorescence signals were quantified in FIG. 6B.

Figure 7A:
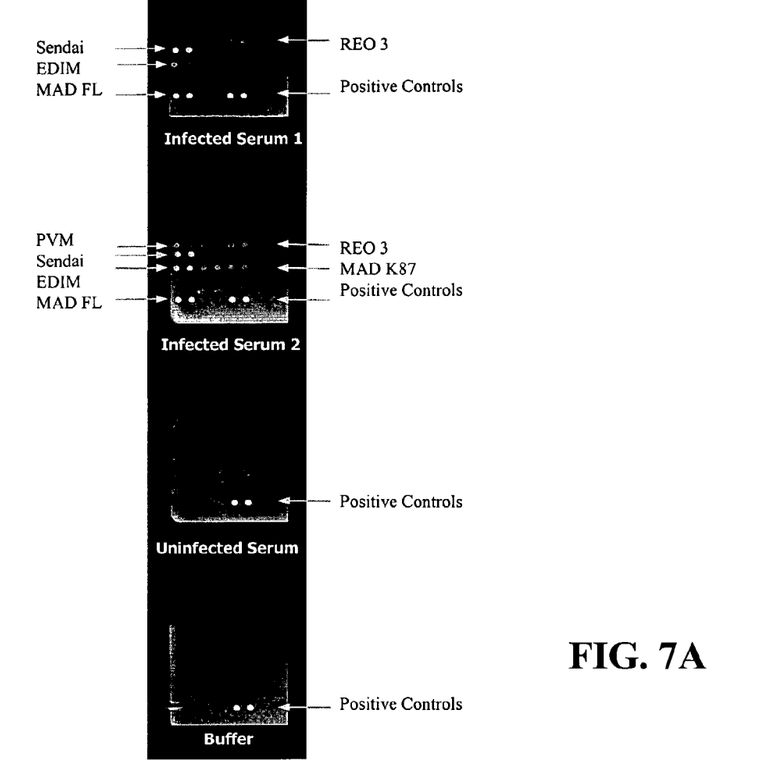
FIG. 7A shows images of mouse surveillance microarrays exposed to different serum and control samples. The images were captured using a SpotWare scanner (TeleChem International, Sunnyvale, Calif.).
Figure 7B:
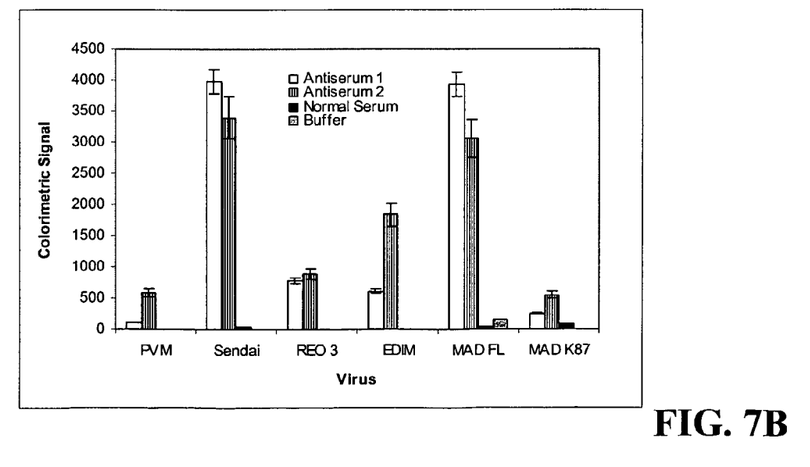
FIG. 7B is the quantification analysis of the images in FIG. 7A with a commercially available software—GenePix Pro 4.0 (Axon Instruments, Union City, Calif.). Colorimetric signals of each viral infection are averaged upon duplicate spots.

In the next set of experiments, two cocktails of mouse antisera, designated Infected Mouse Serum 1 and 2, were prepared by mixing 4 and 6 different mouse antisera, respectively. Specifically, Infected Mouse Serum 1 contains antisera to Sendai virus, EDIM, mouse adenovirus FL (MAD FL) and REO3; and Infected Mouse Serum 2 contains antisera to PVM, Sendai, EDIM, MAD FL, REO3, and mouse adenovirus K87 (MAD K87). After a 15-minute incubation with a Tris-buffer (pH 7.2) to wash away non-bounded antigens, the mouse surveillance microarray was incubated with either Infected Mouse Serum 1 or Infected Mouse Serum 2 for 2 hour at the room temperature to evaluate the specificity of assays. The microarrays were then washed with Tris-buffered saline, pH7.2, incubated for 1 hour at the room temperature with a biotinylated or horseradish peroxidase (HRP) labeled secondary antibody specific for mouse IgG was incubated with the arrays for 1 hour, followed by an incubation with Straptavidin-Cy5 or HRP color substrate for generation of binding signals. The fluorescence or color image was captured by a fluorescent or colorimetric scanner and analyzed with image analysis software. The volume of sample or reagent required in each step was 35 µl per microarray. FIG. 7A shows results of mouse surveillance microarray detected by a colorimetric scanner. Signals were developed only on the viral spots interacted with existing specific antibodies in infected sera. There were little signals on array incubated with health mouse serum other than positive controls. The results were quantitated in FIG. 7B.

Taken together, these results suggest that the mouse surveillance microarray provides specific detection of antisera to a variety of viral antigens. The microarrays can be used to simultaneously detect multiple viral infections in mouse sera. Moreover, the multiplexed and inexpensive assay may be completed in about three hours with small amounts of samples or reagents and in potentially automatic and high-throughput modes.

Example 3

Figure 8A:
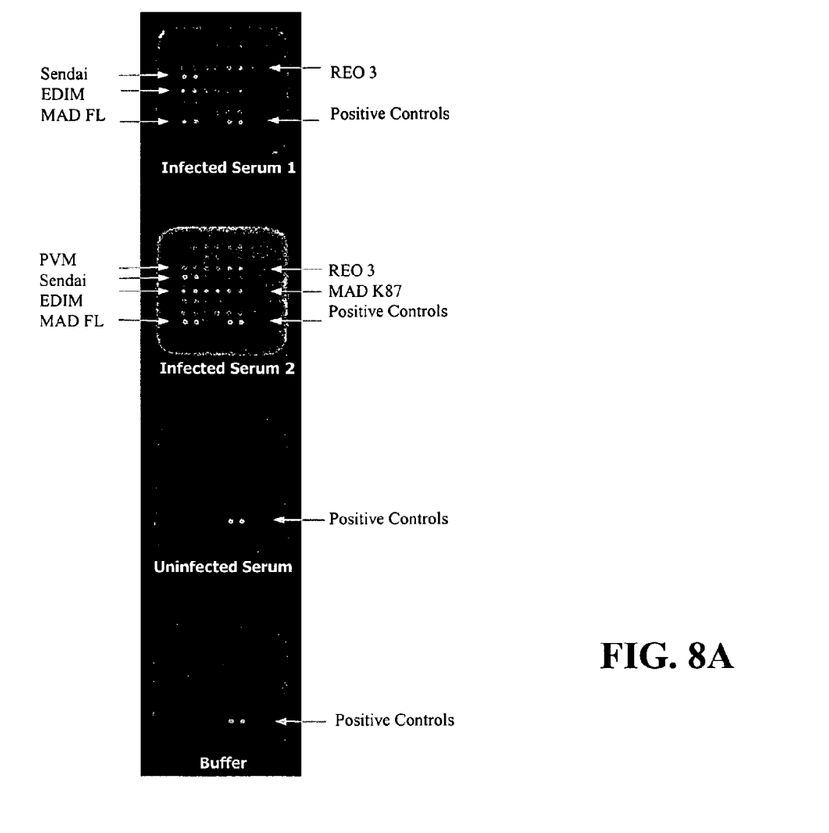
FIG. 8A shows images of mouse surveillance microarrays exposed to different mouse serum and control samples. The microarray was designed as shown in FIG. 1 except for positive controls.
Figure 8B:
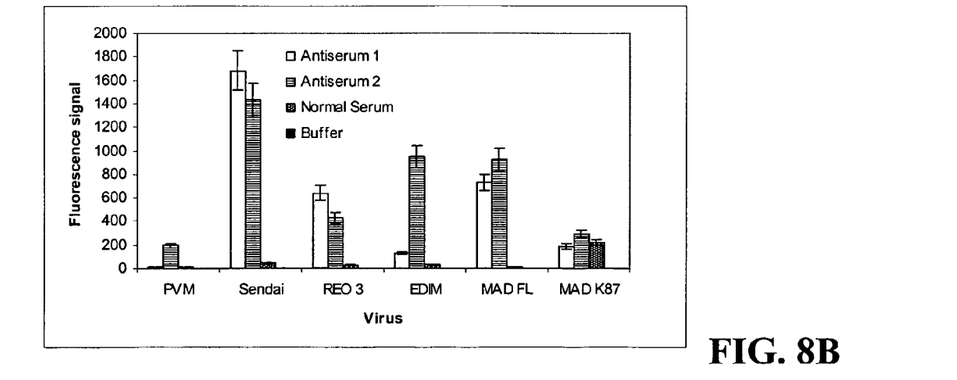
FIG. 8B is a quantitative analysis of the microarray of FIG. 8A with GenePix Pro 4.0 (Axon Instruments, Union City, Calif.).
Figure 9A:
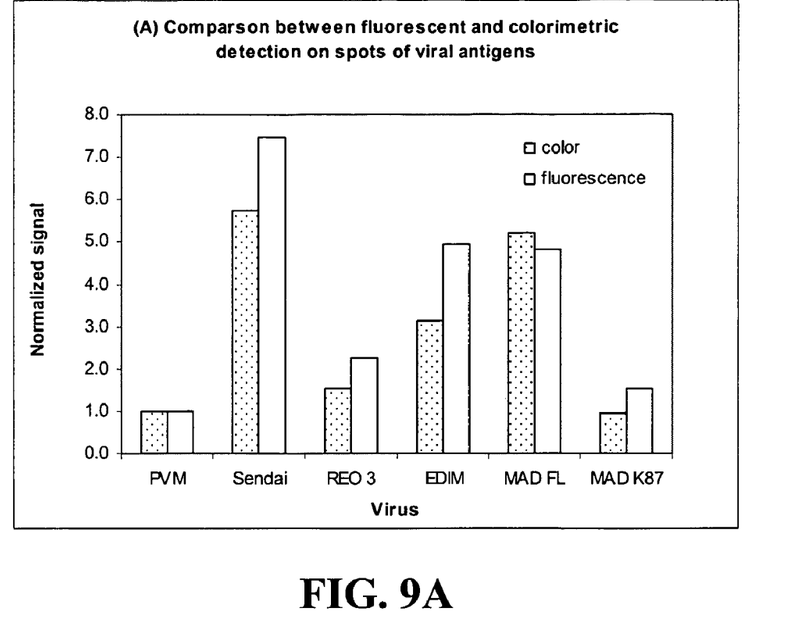
FIG. 9A shows positive signals normalized upon spots of the PVM viral antigen (P3).
Figure 9B:
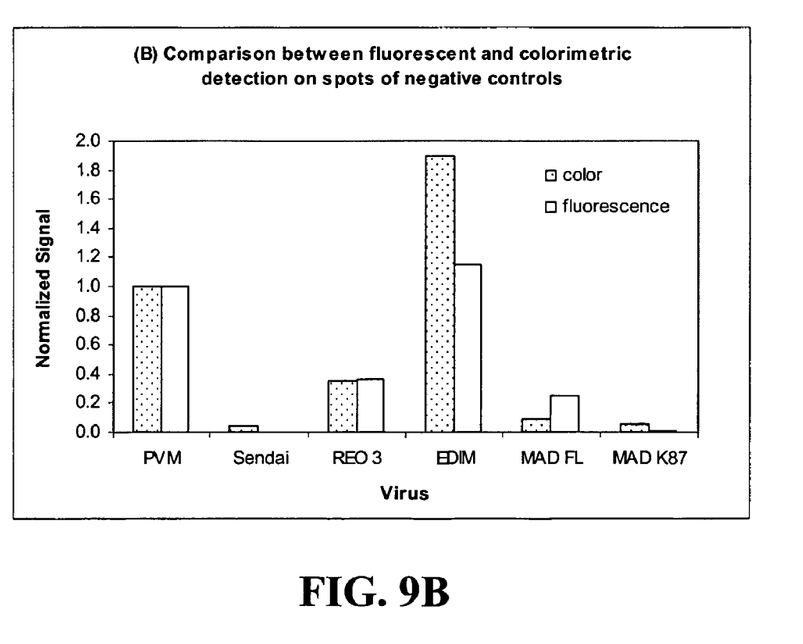
FIG. 9B shows signals that are normalized upon spots of the negative control of PVM viral antigen (N3).

Multiplexed Detection of Animal Viral Infection Using Fluorescent and Colorimetric Microarray Assays In this experiment, two identical antigen microarray slides were used for colorimetric and fluorescent detection, respectively. The antigen microarrays were incubated with Infected Mouse Serum 2 for 1 hour at room temperature, followed by incubation with HRP labeled goat anti-mouse antibody (calorimetric slide) or biotinylated goat anti-mouse antibody (fluorescent slide) for 1 hour at room temperature, and then with HPR color substrate (calorimetric slide) or Streptavidin-Cy5 (fluorescent slide) for 30 minutes. Assay images were captured by a fluorescent laser scanner—ScanArray 3000 (General Scanning, Watertown, Mass.) or calorimetric CCD scanner—VisionSpot (Allied Biotech, Ijamsville, Md.). Quantification analysis of captured images was performed using commercial available software—GenePix Pro 4.0 (Axon Instruments, Union City, Calif.). Signals were averaged upon duplicated spots of each viral antigen and its negative controls. FIGS. 8A and 8B show the fluorescent image of the microarray and relative signal strength, respectively. As shown in FIGS. 9A and 9B, the inexpensive calorimetric method achieved similar assay sensitivity and specificity for microarray imaging as fluorescent detection demonstrated in FIGS. 8A and 8B.

Example 4

Multiplexed Detection of Animal Viral Infection Using Bead-Based Immunoassays

Multiplex immunoassays for simultaneous measurement of multiple animal viral infections in a single assay was achieved using bead-based arrays, where viral antigens were immobilized on the different fluorescent labeled beads and assay was detected by a bead reader.

Figure 10:
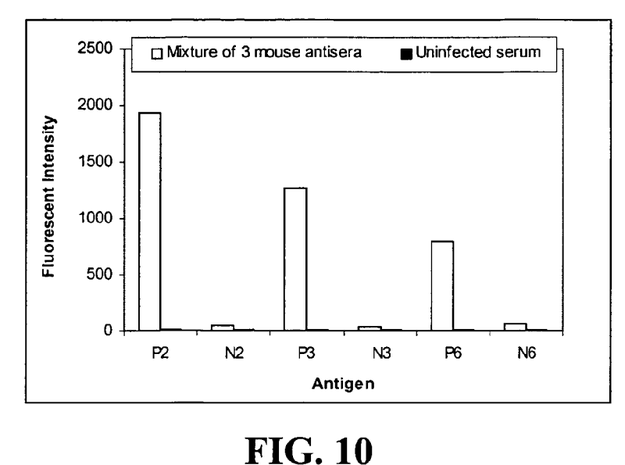
FIG. 10 shows multiplex detection of mouse antisera with beads-based assays. A Luminex 100 beads reader was used for data acquisition and analysis. Mouse viral antigens and negative controls were immobilized in different color-coated beads (Luminex, Austin, Tex.). Mouse antisera were incubated with the beads, followed by incubation of biotinylated goat anti-mouse, and streptavidin-PE conjugate.

A Bio-Plex Amine Coupling Kit (Bio-Rad, Hercules, Calif.) was used to immobilize viral antigens (Charles River, Wilmington, Mass.) on Bio-Plex COOH (Carboxylated) Beads (Luminex, Austin, Tex.) and the procedure in the kit was followed for bead activation and viral antigen coupling. The bead assays were running on the Luminex 100 bead reader (Luminex, Austin, Tex.) with data acquisition and analysis software from Applied Cytometry System, Sacramento, Calif. Briefly, Pre-wet 96-well filter plate with assay buffer in the Bio-Plex Cytokine Assay Kit (Bio-Rad, Hercules, Calif.). The buffer was removed by filter plate vacuum manifold (Millipore, Billerica, Mass.). The multiplex bead working solution was vortexed and pipetted into each well. Non-conjugated antigens and buffer was then removed. The anti-virus antibodies in the antisera were detected through a procedure containing three incubations with the bead at room temperature, and three washing steps, one after each incubation. The three incubations are: (1) incubate the beads with mouse antisera (Charles River, Wilmington, Mass.) for 1 hour; (2) incubate biotinylated goat anti-mouse with the beads for 30 min; and (3) incubate streptavidin-PE with the beads for 10 min. The beads were washed after each incubation and read by a Luminex 100 microplate reader in the 96-well filter plate. Table 2 summarized the bead assay results for multiplex detection of three mouse viral infections, where P2, P3, and P6 denote the positive antigens and N2, N2 and N6 denote negative antigens as described in Table 1; mixture of mouse antisera (2, 3, 6) refers to mixture of mouse antisera specific for antigens P2, P3 and P6. The assay results shown in Table 2 and FIG. 10 indicate successful detection of the three mouse viral infections in a mixture of three mouse antisera using bead-based multiplex assays.

|  | Row | | | |
| --- | --- | --- | --- | --- |
| Column | 7 | 8 | 9 | 10 |
| Plate Layout of Antigen Coated Beads | | | | |
| B | P2 + P3 + P6 | P2 + P3 + P6 | N2 + N3 + N6 | N2 + N3 + N6 |
| C | P2 + P3 + P6 | P2 + P3 + P6 | N2 + N3 + N6 | N2 + N3 + N6 |
| Plate Layout of Mouse antisera Loading | | | | |
| B | Mixture of antisera (2, 3, 6) | Mixture of antisera (2, 3, 6) | Mixture of antisera (2, 3, 6) | Uninfected Mouse serum |

-continued

| Column | Row | | | |
|---|---|---|---|---|
| | 7 | 8 | 9 | 10 |
| C | Mixture of antisera (2, 3, 6) | Uninfected Mouse serum | Uninfected Mouse serum | Uninfected Mouse serum |

Fluorescent Signal Layout of Mouse antiserum 2

| | | | | |
|---|---|---|---|---|
| B | 2181 | 2335 | 49 | 11 |
| C | 1305 | 19 | 9 | 9 |

Fluorescent Signal Layout of Mouse antiserum 3

| | | | | |
|---|---|---|---|---|
| B | 1375 | 1513 | 43 | 9 |
| C | 915 | 7 | 7 | 9 |

Fluorescent Signal Layout of Mouse antiserum

| | | | | |
|---|---|---|---|---|
| B | 805 | 969 | 67 | 17 |
| C | 605 | 7 | 11 | 5 |

Example 5

Multiplex detection of mouse viral infection using 96-well microplate-based microarrays Multiplex detection of multiple mouse viral infections was achieved using 96-well microplate-based microarrays, where mouse viral antigens were immobilized on the bottom of a well. The positive mouse viral antigens, P1 (16 ug/ml in PBS), P2 (16 ug/ml in PBS), and P5 (19 ug/ml in PBS), and relevant negative controls, N1 (16 ug/m in PBS), N2 (16 ug/ml in PBS), and N5 (19 ug/ml in PBS) as described in Table 1 were deposited on wells of a black with clear bottom, polystyrene Corning Costar 3712 plate (Corning, Acton, Mass.) using Radius 3XVP spotter (Radius Biosciences, Gaithersburg, Md.). The array design was shown in FIG. 11(A). Spotted plate-arrays were kept in 4° C. for overnight.

Prior to loading infected mouse antisera (Churchill Applied Biotechnology Ltd, UK), the plate-arrays were incubated with PBS wash buffer (pH 7.2, Tween-20 0.2%) for 3 times and. The mouse antisera (P2 & P5) at dilution of 1:100 in PBS (pH 7.2) were incubated with the arrays (40 ml per well) for 2 hours. Biotinylated secondary antibody specific for mouse IgG was incubated with the arrays for 1 hour. Straptavidin-Cy5 was added to the arrays for fluorescence development of binding spots. Fluorescence images of plate-arrays were captured by AlphaArray 7000 (Alpha Innotech, San Leandro, Calif.), and GenePix 4.0 (Axon Instruments, Union City, Calif.) was used for array image analysis.

Figure 11A:
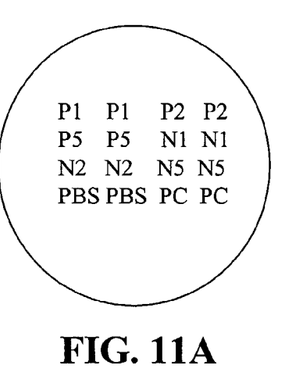
FIG. 11A shows a 4×4 subarray design in a well. P1, P2, P5, N1, N2, N5 are described in Table 1. PBS and PC are negative and positive controls, respectively.
Figure 11B:
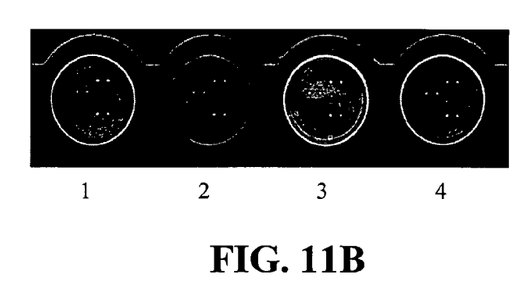
FIG. 11B shows plate-array image in 4 wells under different assay conditions.
Figure 11C:
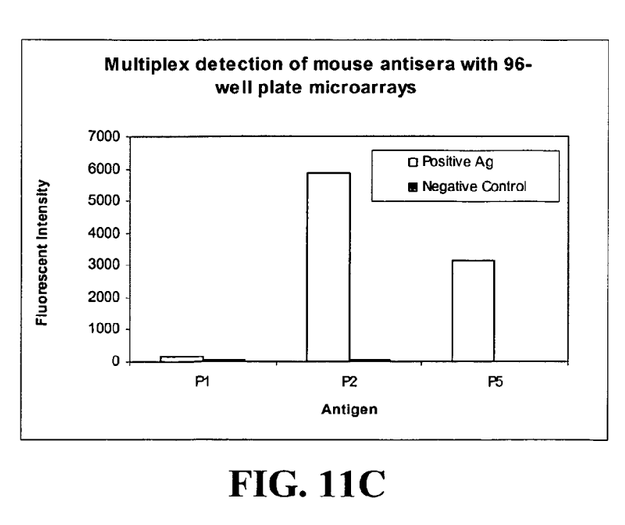
FIG. 11C shows the assay results in terms of fluorescent intensity.

FIG. 11 shows the assay results of plate-arrays indicating successful detection of 2 mouse viral infections (P2 and P5) simultaneously. There are little fluorescent signals developed for negative controls and P1 antigen spots, which confirms assay specificity of the plate-based microarrays for multiplex detection of mouse antisera.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto. All of the documents cited in this application are incorporated by reference in their entirety. Additionally, all sequences cited in databases and all references disclosed are incorporated by reference in their entirety.

What is claimed is:

1. A microarray system for detection of viral infection in a subject, said microarray system comprising a plurality of subarrays fabricated on a solid support, each subarray comprising a plurality of anti-ligands immobilized to said solid support,
    wherein each subarray comprises anti-ligands capable of specific binding to anti-virus antibodies against MHV, MVM, PVM, TMEV, EDIM, MSGV, LCM, Sendai virus, polyoma virus, Extromelia virus, murine herpesvirus, and murine adenovirus,
    wherein said solid support is a microtiter plate and wherein each subarray is located at a bottom of a well.

2. The microarray system of claim 1, wherein said a plurality of anti-ligands are immobilized to said solid support through covalent bonding.

3. The microarray system of claim 1, wherein said a plurality of anti-ligands are immobilized to said solid support through non-covalent bonding.

4. A kit for detection of viral infection in a subject, said kit comprising:
    the microarray system of claim 1; and
    a labeling reagent capable of binding to said anti-virus antibodies.

5. The kit of claim 4, wherein the labeling reagent comprising an anti-ligand conjugated to a detectable tag.

6. The microarray system of claim 1, further comprising a bar code.

7. The microarray system of claim 1, wherein said anti-ligands comprise viral antigens.

8. The microarray system of claim 7, wherein said viral antigens comprise protein antigens.

9. A microarray system for detection of viral infection in a subject, said microarray system comprising a plurality of subarrays fabricated on a solid support, each subarray comprising a plurality of anti-ligands immobilized to said solid support,
    wherein each subarray comprises anti-ligands capable of specific binding to viral antigens from MHV, MVM, PVM, TMEV, EDIM, MSGV, LCM, Sendai virus, polyoma virus, Extromelia virus, murine herpesvirus, and murine adenovirus,
    wherein said solid support is a microtiter plate and wherein each subarray is located at a bottom of a well.

10. The microarray system of claim 9, wherein said a plurality of anti-ligands are immobilized to said solid support through covalent bonding.

11. The microarray system of claim 9, wherein said a plurality of anti-ligands are immobilized to said solid support through non-covalent bonding.

12. The microarray system of claim 9, further comprising a bar code.

13. The microarray system of claim 9, wherein said viral antigens comprise protein antigens.

14. The microarray system of claim 9, wherein said anti-ligands comprise anti-virus antibodies.

* * * * *